US00PP36120P3

(12) United States Plant Patent
Pieters

(10) Patent No.: US PP36,120 P3
(45) Date of Patent: Sep. 17, 2024

(54) ***CHRYSANTHEMUM* PLANT NAMED 'Josarama'**

(50) Latin Name: ***Chrysandthemum* X *morifolium***
Varietal Denomination: Josarama

(71) Applicant: PIETERS JOSEPH & LUC B.V., Staden-Oostnieuwkerke (BE)

(72) Inventor: Christophe Pieters, Staden-Oostnieuwkerke (BE)

(73) Assignee: PIETERS JOSEPH + LUC B.V., Staden-Oostnieuwkerke (BE)

( * ) Notice: Subject to any disclaimer, the term of this patent is extended or adjusted under 35 U.S.C. 154(b) by 0 days.

(21) Appl. No.: 18/527,274

(22) Filed: Dec. 2, 2023

(65) Prior Publication Data

US 2024/0188461 P1 Jun. 6, 2024

Related U.S. Application Data

(60) Provisional application No. 63/430,011, filed on Dec. 3, 2022.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05)

(58) Field of Classification Search
USPC ..... Plt./287, 292
CPC ..... A01H 5/02; A01H 5/00; A01H 6/1424; A01H 6/14
See application file for complete search history.

(56) References Cited

U.S. PATENT DOCUMENTS

PP30,192 P2 * 2/2019 Pieters ..... A01H 6/1424 Plt./291

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'Josarama', characterized by its relatively compact, upright, outwardly spreading and uniformly rounded plant habit; vigorous growth habit; freely branching habit; dense and full plant habit; medium green-colored leaves; early, uniform and freely flowering habit; decorative type inflorescences with ray florets that are dark purplish red in color; relative resistance to Fusarium Wilt, White Rust and Verticillium Wilt; and good greenhouse and outdoor performance.

2 Drawing Sheets

Figure 1:
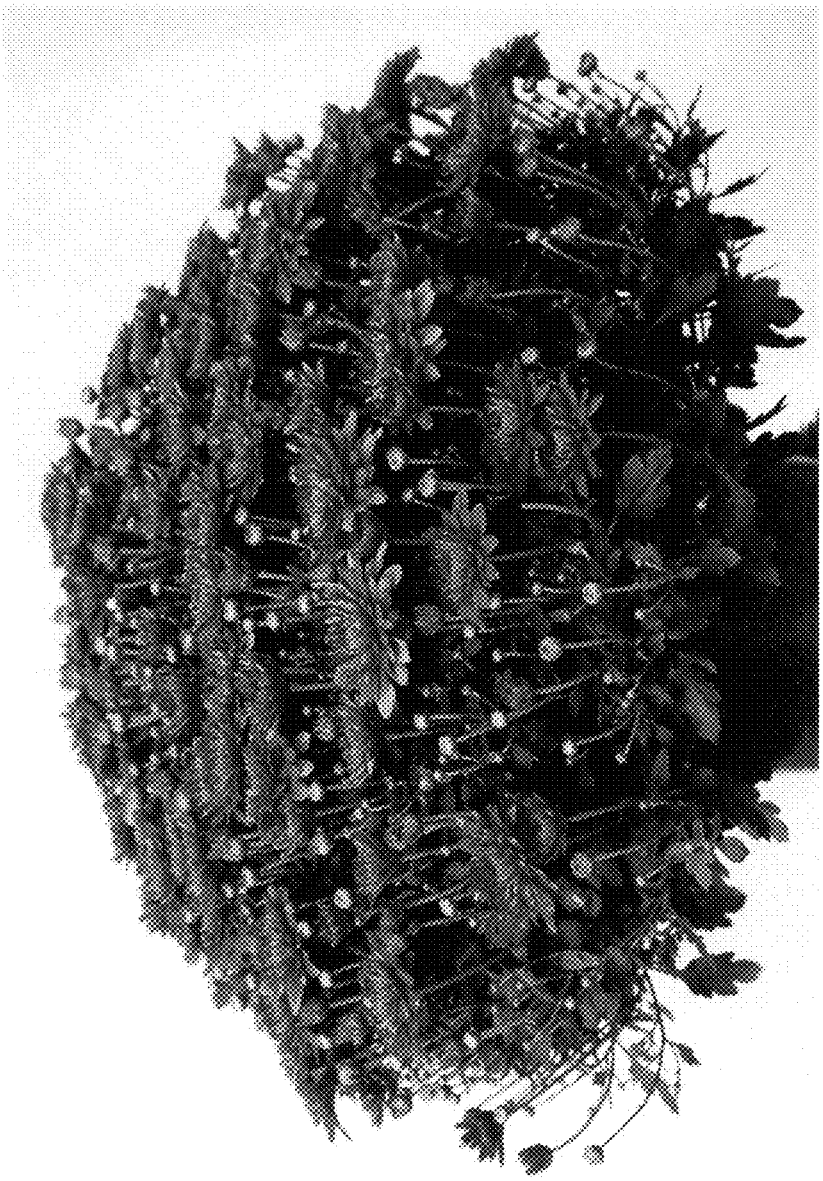

Botanical designation: *Chrysanthemum* X *morifolium*.
Cultivar denomination: 'JOSARAMA'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Pieters Joseph & Luc B.V. of Staden-Oostnieuwkerke, Belgium on Jan. 17, 2022, application number 2022/0150. Foreign priority is not claimed to this European Community Plant Breeder's Rights application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* X *morifolium* and hereinafter referred to by the name 'Josarama'.

The new *Chrysanthemum* plant is a product of a planned breeding program conducted by the Inventor in Staden-Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination conducted by the Inventor in Staden-Oostnieuwkerke, Belgium in October, 2013 of *Chrysanthemum* X *morifolium* 'JO44MAU', not patented, as the female, or seed, parent and *Chrysanthemum* X *morifolium* 'Mefisto Purple', disclosed in U.S. Plant Pat. No. 21,896, as the male, or pollen, parent. The new *Chrysanthemum* plant was discovered and selected by the Inventor as a single flowering plant from within the progeny of the stated cross-pollination grown in a controlled greenhouse environment in Staden-Oostnieuwkerke, Belgium in October, 2014.

Asexual reproduction of the new *Chrysanthemum* plant by vegetative terminal cuttings was first conducted in a controlled greenhouse environment in Staden-Oostnieuwkerke, Belgium in February, 2015. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Josarama'. These characteristics in combination distinguish 'Josarama' as a new and distinct *Chrysanthemum* plant:

1. Relatively compact, upright, outwardly spreading and uniformly rounded plant habit.
2. Vigorous growth habit.
3. Freely branching habit; dense and full plant habit.
4. Medium green-colored leaves.
5. Early, uniform and freely flowering habit.
6. Decorative type inflorescences with ray florets that are dark purplish red in color.
7. Relative resistant to Fusarium Wilt, White Rust and Verticillium Wilt.
8. Good greenhouse and outdoor performance.

Plants of the new *Chrysanthemum* can be compared to plants of the female parent, 'JO44MAU'. In side-by-side comparisons, plants of the new *Chrysanthemum* differ primarily from plants of 'JO44MAU' in the following characteristics:

1. Plants of the new *Chrysanthemum* are more compact than plants of 'JO44MAU'.
2. Inflorescences of plants of the new *Chrysanthemum* have more ray florets and are denser than inflorescences of plants of 'JO44MAU'.
3. Plants of the new *Chrysanthemum* flower earlier than plants of 'JO44MAU'.

Plants of the new *Chrysanthemum* can be compared to plants of the male parent, 'Mefisto Purple'. In side-by-side comparisons, plants of the new *Chrysanthemum* differ primarily from plants of 'Mefisto Purple' in the following characteristics:

1. Plants of the new *Chrysanthemum* are more outwardly spreading than and not as upright as plants of 'Mefisto Purple'.
2. Plants of the new *Chrysanthemum* flower earlier than plants of 'Mefisto Purple'.

Plants of the new *Chrysanthemum* can be compared to plants of *Chrysanthemum* X *morifolium* 'Josaradpi', disclosed in a U.S. Plant patent application Ser. No. 18/527,280 filed concurrently. In side-by-side comparisons, plants of the new *Chrysanthemum* differ primarily from plants of 'Josaradpi' in ray floret color as plants of the new *Chrysanthemum* are dark purplish red in color whereas ray florets of plants of 'Josaradpi' are reddish purple in color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering plant of 'Josarama' grown in a container.

Figure 2:
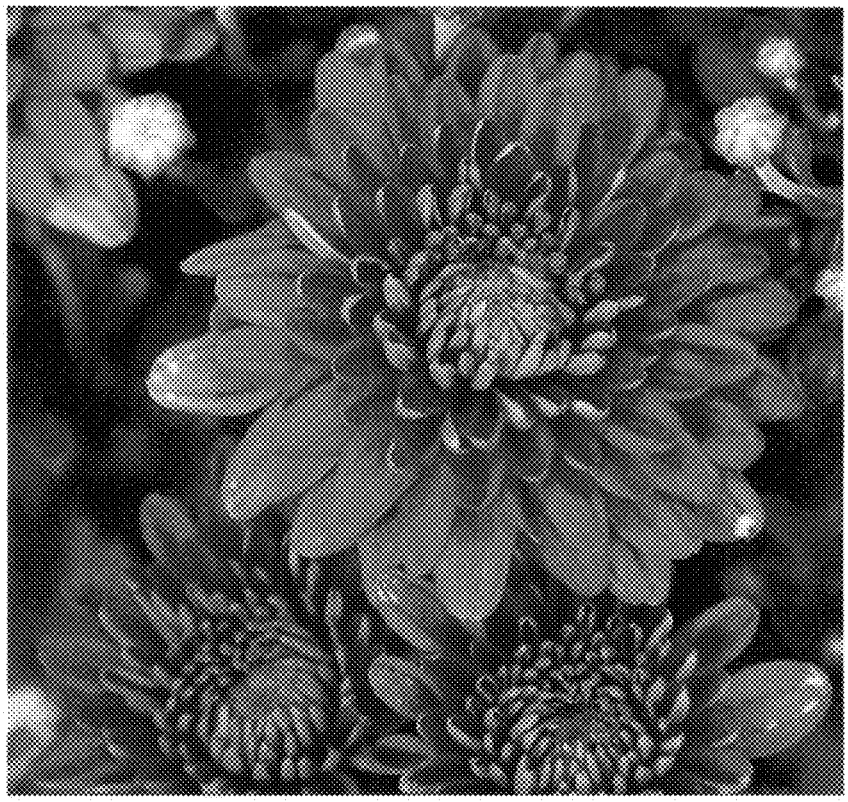

The photograph on the second sheet (FIG. 2) is a close-up view of a typical flowering plant of 'Josarama'.

DETAILED BOTANICAL DESCRIPTION

The aforementioned photographs and following observations and measurements describe plants grown in 19-cm containers in an outdoor nursery in Staden-Oostnieuwkerke, Belgium under natural daylengths during the autumn and employing cultural practices typically used in commercial *Chrysanthemum* production. During the production of the plants, day temperatures ranged from 10C to 25C and night temperatures ranged from 5C to 15C. Plants were 3.5 months old when the photographs and detailed description were taken. In the following description, color references are made to The Royal Horticultural Society Colour Chart, 2015 Edition, except where general terms of ordinary dictionary significance are used.

Botanical classification: *Chrysanthemum* X *morifolium* 'Josarama'.

Parentage:

*Female, or seed, parent.*—*Chrysanthemum* X *morifolium* 'JO44MAU', not patented.

*Male, or pollen, parent.*—*Chrysanthemum* X *morifolium* 'Mefisto Purple', disclosed in U.S. Plant Pat. No. 21,896.

Propagation:

*Type cutting.*—By vegetative tip cuttings.

*Time to initiate roots, summer.*—About 14 days at temperatures about 20C.

*Time to initiate roots, winter.*—About 20 days at temperatures about 20C.

*Time to produce a rooted young plant, summer.*—About three weeks at temperatures about 20C.

*Time to produce a rooted young plant, winter.*—About four weeks at temperatures about 20C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Appearance.*—Perennial decorative type *Chrysanthemum*; plants relatively compact, upright to outwardly spreading giving a uniformly rounded appearance to the plant; plants roughly spherical and flattened globular in overall shape; very freely branching habit with about seven primary lateral branches, each primary lateral branch with about nine secondary branches; pinching is not required, but will enhance lateral branch development; dense and full plant habit; vigorous growth habit and rapid growth rate; plants flexible, not brittle.

*Plant height, soil level to top of foliar plane.*—About 30.8 cm.

*Plant height, soil level to top of floral plane.*—About 32.5 cm.

*Plant width.*—About 56 cm.

*Lateral branches.*—Length: About 16.8 cm. Diameter: About 3.5 mm. Internode length: About 2 cm. Strength: Strong. Aspect: Erect to about 25 degrees from vertical. Texture and luster: Densely pubescent;

slightly glossy. Color, developing: Close to 138A and 138B. Color, developed: Close to 144A; ridges, close to 152A.

*Leaves.*—Arrangement: Alternate, simple. Length: About 5.6 cm. Width: About 3.7 cm. Shape in overall outline: Broadly ovate to broadly oblong. Apex: Abruptly acute. Base: Long attenuate. Margin: Palmately lobed and coarsely dentate-serrate, sinuses between lateral lobes divergent and medium in depth. Texture and luster, upper surface: Moderately pubescent; slightly glossy. Texture and luster, lower surface: Densely pubescent; matte to slightly glossy. Venation: Palmately reticulate. Color: Developing leaves, upper surface: Close to 137A. Developing leaves, lower surface: Close to 147B. Fully expanded leaves, upper surface: Close to NN137B; venation, close to 146A. Fully expanded leaves, lower surface: Close to 147B; venation, close to 148B. Petioles: Length: About 1 cm. Diameter: About 1.75 mm to 2 mm. Strength: Moderately strong. Texture and luster, upper surface: Moderately to densely pubescent; slightly glossy. Texture and luster, lower surface: Densely pubescent; slightly glossy. Color, upper surface: Close to 146B; at the marginal edges, close to NN137B. Color, lower surface: Close to 148C; at the marginal edges, close to 147B. Stipules: Length: About 6 mm. Diameter: About 3 mm. Shape: Ovate. Apex: Short acuminate. Base: Broadly cuneate. Texture, upper surface: Moderately pubescent. Texture, lower surface: Densely pubescent. Color, upper surface: Close to NN137B. Color, lower surface: Close to 147B.

Inflorescence description:

*Appearance.*—Decorative type inflorescence form; inflorescences borne on terminals above foliar plane; disc and ray florets arranged acropetally on a capitulum.

*Fragrance.*—Moderately fragrant, pungent.

*Flowering response.*—Early and long flowering time; under natural season conditions, plants flower during the autumn into the winter in Belgium; flowering response time, about 45 days.

*Postproduction longevity.*—Inflorescences maintain good color and substance for about two weeks; inflorescences persistent.

*Quantity of inflorescences.*—About 21 inflorescences per lateral branch and about 1,325 inflorescences develop per plant.

*Inflorescence buds.*—Height: About 1 cm. Diameter: About 1 cm. Shape: Close to globular. Texture and luster: Smooth, glabrous; towards the base, moderately to densely pubescent; slightly glossy. Color: Immature involucral bracts, close to 143A and 143B and at the marginal edges, close to 145B; immature ray florets, close to a blend of 70B and N77B.

*Inflorescence diameter.*—About 6.5 cm.

*Inflorescence depth (height).*—About 2.2 cm.

*Disc diameter.*—About 1.2 cm.

*Receptacle height.*—About 4 mm.

*Receptacle diameter.*—About 6 mm.

*Receptacle shape.*—Flattened globular.

*Receptacle color.*—Close to 146D; at the center, close to 145B and 145C.

*Ray florets.*—Number of ray florets per inflorescence: About 160 arranged in about six whorls. Length: About 1.3 cm to 3.1 cm. Width: About 7 mm. Shape: Narrowly obovate to narrowly elliptic; initially, slightly to moderately concave becoming slightly to moderately convex with development. Apex: Obtuse. Base: Attenuate. Margin: Entire; fused at the base. Aspect: Depending on development, that is, position on receptacle, about 10 to 65 degrees from horizontal. Texture and luster, upper surface: Smooth, glabrous; slightly velvety; matte. Texture and luster, lower surface: Smooth, glabrous; slightly velvety; slightly glossy. Color: When opening, upper surface: Close to 71A. When opening, lower surface: Close to N74C and 75B. Fully opened, upper surface: Close to 71B; with subsequent development, color becoming closer to a blend of 75C and 201C and proximally, closer to 70B; venation, similar to lamina colors. Fully opened, lower surface: Close to 75A, 75B and N75A; venation, close to N77B; colors do not change with subsequent development.

*Disc florets.*—Number of disc florets per inflorescence: About 80 spirally arranged at the center of the inflorescence. Length: About 7 mm. Diameter: About 2 mm. Shape: Tubular; apices acute. Texture and luster, inner surface: Smooth, glabrous; slightly velvety; slightly glossy. Texture and luster, outer surface: Smooth, glabrous; slightly velvety; glossy. Color, developing, inner and outer surfaces: Apex: Close to 14A. Mid-section and base: Close to 145C. Color, developed, inner and outer surfaces: Apex: Close to 13A. Mid-section and base: Close to 145C.

*Phyllaries.*—Number of phyllaries per inflorescence: About 30 arranged in three whorls. Length: About 9 mm. Width: About 2.5 mm. Shape: Ovate to narrowly ovate. Apex: Bluntly acute. Base: Cuneate. Margin: Entire; translucent. Texture and luster, upper surface: Smooth, glabrous; moderately glossy. Texture and luster, lower surface: Moderately to densely pubescent; slightly glossy. Color, upper surface: Close to 143C; marginal edges, close to 145D; apex, close to 199A and 199B. Color, lower surface: Close to 143A; marginal edges, close to 144C; apex, strongly tinged with close to 199A and 199B.

*Peduncles.*—Length, terminal peduncle: About 3.8 cm. Length, third peduncle: About 3.4 cm. Diameter, terminal and third peduncles: About 2 mm. Aspect, terminal peduncle: Mostly erect. Aspect, third peduncle: About 30 degrees from vertical. Strength: Strong. Texture and luster: Moderately to densely pubescent; moderately glossy. Color: Close to 138B.

*Reproductive organs.*—Androecium: Only present on disc florets. Quantity per disc floret: About five. Filament length: About 3 mm. Filament color: Close to 145C. Anther size: About 0.5 mm by 2 mm. Anther shape: Linear. Anther color: Close to 13A. Pollen amount: Scarce. Pollen color: Close to 15A. Gynoecium: Present on ray and disc florets. Quantity per floret: One. Pistil length: About 6 mm. Stigma diameter: About 0.2 mm. Stigma shape: Cleft, decurrent. Stigma color: Close to 13A. Style length: About 5 mm. Style color: Close to 145C and 145D. Ovary color: Close to 157A.

*Seeds and fruits.*—To date, seed and fruit production have not been observed on plants of the new *Chrysanthemum.*

Garden performance: Plants of the new *Chrysanthemum* have demonstrated good garden performance and will tolerate temperatures ranging from about −12C to about 35C and to be suitable for USDA Hardiness Zones 8 to 10.

Pest & pathogen resistance: Plants of the new *Chrysanthemum* have been observed to have relative resistance to Fusarium Wilt (*Fusarium oxysporum*), White Rust (*Puccinia horiana*) and Verticillium Wilt (*Verticillium alboatrum*). Plants of the new *Chrysanthemum* have not been observed to be resistant to pests and other pathogens of *Chrysanthemums*.

It is claimed:

1. A new and distinct *Chrysanthemum* plant named 'Josarama' as illustrated and described.

* * * * *